United States Patent [19]

Vogel et al.

[11] 4,283,221

[45] * Aug. 11, 1981

[54] PLANT GROWTH REGULATING AGENT

[75] Inventors: Christian Vogel, Binningen; Rudolf Aebi, Basel, both of Switzerland

[73] Assignee: Ciba-Geigy Corporation, Ardsley, N.Y.

[ * ] Notice: The portion of the term of this patent subsequent to Feb. 10, 1993, has been disclaimed.

[21] Appl. No.: 688,868

[22] Filed: May 21, 1976

Related U.S. Application Data

[63] Continuation-in-part of Ser. No. 548,041, Feb. 7, 1975, abandoned, which is a continuation-in-part of Ser. No. 328,202, Jan. 31, 1973, abandoned.

[30] Foreign Application Priority Data

Feb. 7, 1972 [CH] Switzerland ............... 1739/72
Feb. 16, 1972 [CH] Switzerland ............... 7203/72

[51] Int. Cl.³ ............... A01N 37/22; C07C 103/32
[52] U.S. Cl. ............... 71/118; 71/76; 564/214

[58] Field of Search ............... 71/118, 76; 260/562 B; 564/214

[56] References Cited

U.S. PATENT DOCUMENTS

| 3,442,945 | 5/1969 | Olin | 71/118 X |
|---|---|---|---|
| 3,547,620 | 12/1970 | Olin | 71/118 |
| 3,586,496 | 6/1971 | Chupp | 71/118 |
| 3,739,024 | 6/1973 | Chupp | 260/551 S |
| 3,937,730 | 2/1976 | Vogel et al. | 71/118 X |
| 3,952,056 | 4/1976 | Vogel et al. | 71/118 X |

FOREIGN PATENT DOCUMENTS

| 1903198 | 8/1970 | Fed. Rep. of Germany | 260/562 |
|---|---|---|---|
| 1283163 | 6/1972 | United Kingdom | 71/118 |

*Primary Examiner*—Catherine L. Mills
*Attorney, Agent, or Firm*—Frederick H. Rabin; Harry Falber

[57] ABSTRACT

2-Chloro-2',6'-dimethyl-N-(2-methoxyethyl)-acetanilide is disclosed as plant growth regulating agent with long lasting activity.

4 Claims, No Drawings

PLANT GROWTH REGULATING AGENT

CROSS-REFERENCE

This application is a continuation-in-part of our application Ser. No. 548,041, filed Feb. 7, 1975, now abandoned which in turn is a continuation-in-part of our abandoned application Ser. No. 328,202, filed Jan. 31, 1973.

The present invention relates to 2-chloro-2',6'-dimethyl-N-(2-methoxyethyl)-acetanilide having the formula I

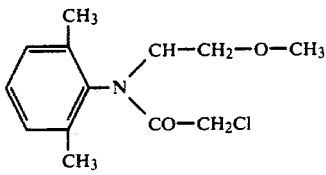

a process for its preparation as well as plant-growth regulating agents containing this compound as active ingredient and to a method for plant growth regulation by use of the new compound.

Various types of haloacetanilides have been described in the art as being herbicidally active.

In U.S. Pat. No. 3,442,945 it is stated that: "It will be noted that the nitrogen-substituted α-haloacetanilides which are nuclear-substituted with a tertiary alkyl group in one ortho-position and another substituent in the other ortho position possess unusual grass specifity and, furthermore, that these α-haloacetanilides have unusually high activity at extremely low application rates."

In accordance with this statement 2'-tert.butyl-2-chloro-N-ethoxyethyl-6'-ethylacetanilide of the formula A

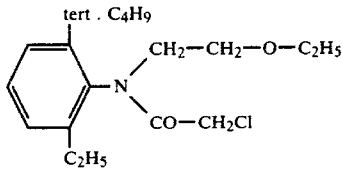

is highlighted inter alia as an example of a compound being especially active at low dosage levels.

U.S. Pat. No. 3,547,620 is also directed to chloracetanilides as "phytotoxicants". This term is used to designate materials having a modifying effect upon the growth or development of vegetation. Such effects include for example killing, retardation, tillering, dwarfing and other deviations from natural development. In example 85 of U.S. Pat. No. 3,547,620 and appendant Table IV it is shown that 2-chloro-2'-tert.butyl-6'-ethyl-N-(ethoxymethyl)acetanilide of the formula A'

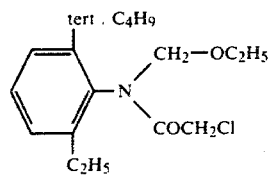

exhibits a 25% improvement in herbicidal activity over that of the above compound A. Further test results in tables V, VI and VII corroborate these findings and following conclusion is drawn:

"The difference in herbicidal effectiveness is directly related to the presence of an alkoxymethyl, instead of an alkoxyethyl or alkoxypropyl group, on the nitrogen atom of the acetanilide. It is immaterial, as is shown in this example, whether the halo is bromine or chlorine."

From the combined teachings of these patents it would follow that chloro- and bromoacetanilides containing an alkoxymethyl rather than an alkoxyethyl group on the nitrogen atom and particularily those with an ortho tert. butyl group are likely to possess the most favourable plant growth regulating and herbicidal activity for practicle purposes. The closest analog described in U.S. Pat. No. 3,547,620 is compound B shown hereinafter.

Furthermore U.S. Pat. No. 3,739,024 shows that the conversion of haloacetanilides with thionophosphine sulfide produces halothioacetanilides having particularily useful herbicidal properties. Halothioacetanilides containing the allegedly herbicidally less advantageous alkoxyethyl group at the nitrogen atom are also exemplified.

It has now been found that the compound of the formula I in contrast to known acetanilide derivatives exhibits long lasting plant growth regulating properties, in particular post emergent growth retarding or inhibiting effects on plants.

2-chloro-2',6'-dimethyl-N-(2-methoxyethyl)-acetanilide acts as a plant-growth regulator in that it delays or inhibits the growth of many mono- or di- cotyledonous plants be they plant cultures or weeds. The primary consequence of this activity is a reduction of the plant size in particular its height. As a direct result of the reduction in height the plant gains in sturdiness, the leaves and stems grow stronger and in the case of cereals a reduction of the internodal distance results in greater resistance to bending and breaking. A further benefit of reduced growth in plant cultures and, for example, lawns, sports fields and other grassed-over areas is the saving in manure and/or fertilizer and in the case of the latter the reduced frequency at which they must be mown or scythed. The prime importance of this property becomes clear when grasses on roadsides, river and canal banks, airports and the like are considered. Under normal circumstances such areas require regular mowing or scything which involves high labour and machinery costs. In addition the danger to the personel working for example beside highways and in airports is considerable.

There is therefore a real need particularly in intensive traffic areas for maintaining, in good condition, the turf essential for preventing erosion whilst at the same time the height of the grass reasonably low over the entire growth period.

The compound I of the instant invention satisfies fully the above requirements and desiderata. In particular it is capable of restricting the growth of grass without in any way affecting the strength or health of the plant itself. In other words the growth regulation is not a result of phytotoxicity.

This is all the more surprising in that close analogs of the instant compound are phytotoxic (herbicidal) and/or considerably less active as growth regulants.

The exceptional nature of this activity is further confirmed by the fact that on preemergent application compound I is highly effective as a selective herbicide.

This invention also relates to a method for the control of axillary shoots on tobacco-plants. It is known that the quality of tobacco leaves is improved by removal of the top portion containing the flower, a process known as topping. The purpose of topping is to direct the energies of the plant which would normally go to the formation of the seed head toward increased leaf development. If at the same time the auxillary shoots (suckers) are not removed or otherwise controlled too much of the plant's energy will be sapped, with the result that low quality leaves will be produced over the whole plant. It is, therefore, one object of this invention to control tobacco suckers by treating the plants with an effective amount of compound I. This compound may also be used to control suckers in tomato plants. The growth retarding activity of compound I can be also be utilized for improving the harvest per unit area of crop cultures such as soybeans, beans, cotton, coffee etc. by reducing the vegetative growth in favor of improved blossoming and fruiting. Moreover, the application of compound I to a crop results in a reduction in plant stature which enables e.g. more intensive planting of soybeans per unit area. A further use to which compound I can be put is the control of shoots in stored potatoes. As in the case of suckers these shoots result in an undesirable waste of energy (starch) which leads to a considerable reduction in nutritional value.

Compound I may of course be used in conjunction with other active substances.

The compound of the formula I may be manufactured by reacting the N-substituted aniline of the formula II

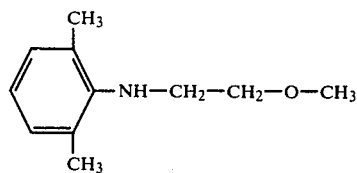

with a chloroacetylating agent, preferably an anhydride or halide of chloroacetic acid.

The compound of the formula I may also be produced by reacting 2,6-dimethyl-aniline with a 2-haloethanol subsequently chloroacetylating the obtained compound of the formula IIa

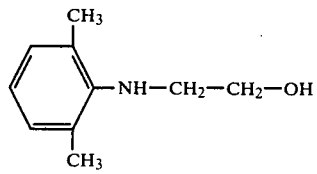

preferably with an anhydride or halide of chloroacetic acid and finally etherifying the free OH group with methanol in acid medium, (e.g. in the presence of HCl, $H_2SO_4$) under mild conditions and in a conventional manner.

The reactions can be carried out in the presence or absence of solvents or diluents which are inert towards the reactants. Examples of suitable solvents or diluents are: aliphatic, aromatic or halogenated hydrocarbons, such as benzene, toluene, xylene, petroleum ether, chlorobenzene, methylene chloride, ethylene chloride, chloroform; ethers and ethereal compounds, such as dialkyl ethers, dioxan, tetrahydrofuran; nitriles, such as acetonitrile; N,N-dialkylated amides, such as dimethyl formamide; also dimethyl sulphoxide, as well as mixtures of these solvents.

Suitable chloroacetylating agents are for example chloroacetic anhydride, and chloroacetic halides, such as chloroacetyl chloride. However, it is also possible to carry out the reaction using chloroacetic acid, or its esters or amides. The reactions are carried out at temperatures between 0° and 200° C., preferably between 20° and 100° C. The chloroacetylation step is usefully carried out in the presence of an acid binding agent (especially if chloroacetyl halides are used). Suitable acid binding agents are: tertiary amines, such as trialkylamines, e.g. triethylamine, pyridine and pyridine bases, or inorganic bases, such as oxides and hydroxides, hydrogen carbonates and carbonates or alkali and alkaline earth metals. Furthermore, it is also possible to use an excess of the corresponding aniline of the formula II as acid binding agent.

Compounds homologous to formula II and hydroxyalkyl derivatives homologous to formula IIa are known, e.g. from U.S. Pat. Nos. 2,381,071, 2,759,943 as well as from Am.Soc. 84, 743 and Bull. Soc. Chim. France 1962, 303 and 1965, 2037.

The starting material of the formula II may be manufactured for example by one of the following known methods:

(a) condensation of 2,6-dimethyl-aniline with methoxyacetaldehyde and simultaneous or subsequent catalytic hydrogenation of the resulting azomethine of the formula III

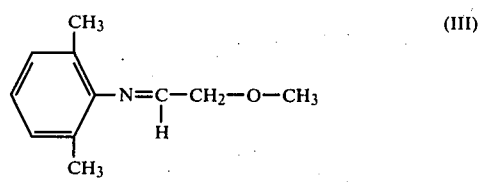

or (b) reaction of 2,6-dimethyl-aniline with a compound of the formula IV $$Y-CH_2-CH_2-O-CH_3 \qquad (IV)$$

wherein Y represents a halogen atom or another anionic group in particular an arylsulphonate radical. Compounds of the formula IV with a benzenesulphonate acid radical as Y are described e.g. in Can. J. Chem. 33, 1207, and those with a tosyloxy radical ($CH_3-C_6-H_4-SO_3-$) in British Pat. No. 869,083.

There are, of course, a number of other processes for the manufacture of the starting materials of the formula II from ortho-alkylated anilines.

The following Examples illustrate the invention:

EXAMPLE 1

(a) Manufacture of the starting material:

A solution of 24.2 (0.2 mole) of 2,6-dimethylaniline and 17.8 g (0.24 mole) of methoxy-acetaldehyde in 150 ml of benzene is treated with 1 ml of 25% trimethylamine solution in methanol and the mixture is refluxed for 5 hours using a steam trap. The reaction mixture is evaporated in vacuo and vacuum distillation of the residue yields the 1-(2'-methoxy-ethylidene-amino)-2,6-dimethylbenzene with a boiling point of 58°–61° C. at 0.1 Torr.

A solution of 16.3 g (0.092 mole) of this intermediate product in 200 ml of absolute ethanol is hydrogenated at 25° C. under normal pressure with the addition of 2 g of 5% palladium charcoal. After filtering off the catalyst and evaporating the filtrate in vacuo, vacuum distillation of the residue yields the N-(2'-methoxyethyl)-2,6-xylidine with a boiling point of 64°–65° C./ 0.2 Torr.

(b) A suspension of 4.4 g of N-(2'-methoxyethyl)-2,6-xylidine and 2.6 g of potassium hydrogen carbonate in 30 ml of absolute benzene is treated dropwise with a solution of 2.94 g of chloroacetyl chloride in 10 ml of benzene, whereupon the mixture is subsequently further stirred for 2 hours at 25° C. For processing it is diluted with 100 ml of ether. The organic phase is wahsed repeatedly with water and dried. The desired 2-chloro-N-(2'-methoxy-ethyl)-2,6-dimethyl-acetanilide is obtained pure and in quantitive yield in the form of an oil by evaporating off the solvent. The compound crystallises on being left to stand at low temperature; m.p. 42°–45° C.

Suitable rates for application of compound I lie between 0.1 and 10 kg per hectare. 2-chloro-2',6'-dimethyl-N-(2-methoxyethyl)-acetanilide of the formula I is markedly superior to the structurally closest known comparative compounds listed below in respect of plant growth regulating properties.

| Comparative compounds | | |
|---|---|---|
| B | CH₃ phenyl-N with CH₂—O—CH₃ and CO—CH₂Cl, CH₃ | No. 29 in U.S. Pat. No. 3,547,620 |
| C | CH₃ phenyl-N with CH₂—CH₂—O—CH₃ and C(=S)—CH₂Cl, CH₃ | according to U.S. Pat. No. 3,739,024 |
| D | CH₃ phenyl-N with CH₂—CH₂—O—CH₃ and CO—CH₂—Br, CH₃ | not known before |
| E | CH₃ cyclohexenyl-N with CH₂—CH₂—O—CH₃ and CO—CH₂Cl, CH₃ | Ex. No. 29 in U.S. Pat. No. 3,586,496 |

Compounds B and C represent the closest state of the art. Compound D is included on the basis of the statement in U.S. Pat. No. 3,547,620 saying that for effectiveness it is immaterial whether the halogen atom in a haloacetanilide is bromine or chlorine.

Comparative compound E belongs to the different chemical class of enamines (cf. A.G. Cook "Enamines", Ed. Marcel Dekker Ltd., New York and London, 1969) and is incorporated in order to show the inferiority of a purely visually similar compound in comparison with compound I of this invention. A description of a process for the preparation of compound E follows.

Preparation of comparative substance E (a) A spatula tip of ammonium chloride is added to a solution of 63 g of 2,6-dimethylcyclohexanone and 37,5 g of 2-methoxyethylamine in 350 ml of dry benzene and the mixture is heated under reflux for 22 hours employing a water separator. The benzene is then distilled off under reduced pressure and the residue fractionally distilled. 57 g of the desired starting material N-(2-methoxy-ethyl)-2,6-dimethyl-cyclohexylideneamine are obtained, b.p. 112°–115° C./20 Torr.

(b) Over a period of 3 hours and at 20°–30° C. 37.5 g of chloroacetylchloride are added dropwise while stirring to a solution of 57 g of N-(2-methoxy-ethyl)-2,6-dimethylcyclohexylideneamine in 200 ml of hexane. Afterwards during 2 hours 48 ml of triethylamine are added dropwise in the course of which the temperature of the mixture rises to ca. 50° C. Subsequently the mixture is heated under reflux for 30 minutes and poured onto ice. The organic layer is washed with water and dried over sodium sulfate. The solvent is distilled off and the residue is fractionally distilled: 54.5 g of N-(2,6-dimethyl-1-cyclohexene-1-yl)-N-(2-methoxyethyl)-α-chloro-acetamide are obtained, b.p. 136°–139° C./0.1 Torr.

EXAMPLE 2

Growth retardation on naturally occuring grasses

Individual naturally grown and well established 1 squaremeter plots of the grasses Dactylis glomerata = orchard grass
Lolium perenne = perennial rye grass
Festuca ovina = red fescue are treated 4 days after their first cutting in early spring with the active substance and covered with a portable greenhouse. Each active substance was applied as a 5% granulate at three different application rates, namely 7,5; 5,0 and 2,5 kg a.s./hectare. Identical untreated plots served as control.

69 days after application evaluation took place according to the following two criteria:
  (i) = growth of grass in cms since application
  (ii) = Phytotoxicity according to the following linear scale
    1 = plants destroyed
    9 = plants undamaged (as control)
    8-2 = intermediate stages Conclusion:

The only substance showing a similar activity is the chemically distinct enamine E which, however, has phytotoxicity which is unacceptable for practical purposes. This phytoxicity is not exhibited by the compound of the invention even at high dosage levels thus minimising the dangers of accidental overdosage which is quite common in practice. The growth regulation activity of compounds B, C and D is inadequate for practical purposes.

| kg a.s. of compound | | (i) growth in cms since application | | | (ii) Phytotoxicity | | |
|---|---|---|---|---|---|---|---|
| | | Dactylis | Lolium | Festuca | Dactylis | Lolium | Festuca |
| B | 7.5 | 9 | 14 | 12 | 9 | 9 | 9 |
| | 5.0 | 17 | 21 | 9 | 9 | 9 | 9 |
| | 2.5 | 22 | 31 | 12 | 9 | 9 | 9 |
| C | 7.5 | 15 | 16 | 9 | 9 | 9 | 9 |

-continued

| kg a.s. of compound | (i) growth in cms since application | | | (ii) Phytotoxicity | | |
|---|---|---|---|---|---|---|
| | Dactylis | Lolium | Festuca | Dactylis | Lolium | Festuca |
| 5.0 | 27 | 21 | 9 | 9 | 9 | 9 |
| 2.5 | 29 | 31 | 9 | 9 | 9 | 9 |
| D 7.5 | 32 | 26 | 12 | 9 | 9 | 9 |
| 5.0 | 42 | 36 | 15 | 9 | 9 | 9 |
| 2.5 | 42 | 46 | 15 | 9 | 9 | 9 |
| E 7.5 | 7 | 6 | 6 | 2 | 2 | 2 |
| 5.0 | 6 | 6 | 6 | 3 | 3 | 4 |
| 2.5 | 15 | 11 | 7 | 9 | 9 | 9 |
| I 7.5 | 3 | 4 | 4 | 8 | 8 | 7 |
| 5.0 | 5 | 3 | 5 | 9 | 9 | 9 |
| 2.5 | 5 | 12 | 12 | 9 | 9 | 9 |
| untreated control | 46 | 47 | 17 | 9 | 9 | 9 |

EXAMPLE 3

Antisprouting activity for potatoes 10 kg samples of previously harvested potatoes of the variety "Bintje" were dipped for one minute in an aqueous broth containing 0.8%, 0.4% or 0.2% of active substance.

After draining the potatoes were stored in chests in an air-conditioned storing room at a temperature of 10° C. and a relative humidity of about 70%. Untreated potatoes served as control.

3 and 5 months after application the average length of the shoots on the tubers was evaluated.

| Concentration of compound I in the broth | length of shoots after | |
|---|---|---|
| | 3 months | 5 months |
| 0.8% | 0 cm | 0 cm |
| 0.4% | 1.5 cm | 2 cm |
| 0.2% | 2 cm | 2 cm |
| untreated control | 7.5 cm | 14 cm |

At lower levels of about 1 to 4 kg a.s. per hectare and on pre-emergent application compound I acts selectively as herbicide in various crop cultures, e.g. in leguminous cultures (soybeans, beans, peas), sugar cane, sunflowers, Brassica species such as rape and cabbage. It exhibits very good weedkilling activity against grasses, such as

*Echinochloa crus galli* = Barnyard grass
*Setaria italica* = Italian foxtail
Digitaria = Crab grass
Lolium = Perennial rye grass
*Avena fatua* = Wild oat
Alopecurus myosuroides = Black grass
Cyperus = Nut grass
Rottboellia = Raoul grass and against many dicotyledonous weeds such as
Amaranthus = Pigweed
Sesbania = Coffeeweed
Chrysanthemum segetum = Corn marigold
Sinapis = mustard
Galium = Cleavers
Ipomoea = Morning glory
Pastinaca = Parsnip Special attention should be drawn to the excellent activity of compound I against Datura (Jimsonweed). Nowadays this weed is a serious hazard in that its seeds which are poisonous contaminate soybeans and the like at harvesting possibly making them unfit for later human consumption (cf. W. B. Ennis, Jr., of USDA, at 1974 meeting of Weed Science Society of America; Abstract 130). By effectively destroying Datura before harvest this problem can be avoided.

EXAMPLE 4

Broad action against dicotyledonous weeds and undesirable grasses on preemergent application Immediately after the test plants have been sown in seed dishes, the active substances are applied to the surface of the soil as an aqueous suspension (obtained from a 25% wettable powder) so as to correspond to rates of application of 4 kg, 2 kg, 1 kg and 0.5 kg per hectare. The seed dishes are then kept at 22° to 23° C. and 70% relative humidity. The test is evaluated according to the linear rating given in Example 2 (— = not tested). The following haloacetanilides known from U.S. patent 3,547,620 acted as comparative compounds: compound A = 2-methyl-6-ethyl-N-(ethoxymethyl)-chloroacetanilide compound B = 2,6-diethyl-N-(methoxymethyl)-chloroacetanilide.

| Compound | application rate in kg/ha | Pastinaca | Galium | Ipomoea | Sinapis | Chrysanthemum | Amaranthus | Sesbania | Echinochloa | Setaria | Digitaria | Rottboellia | Cyperus | Alopecurus | Lolium | Avena | Alfalfa | Soybeans |
|---|---|---|---|---|---|---|---|---|---|---|---|---|---|---|---|---|---|---|
| I | 4 | 1 | 2 | 3 | 2 | 1 | 1 | 1 | 1 | 1 | 1 | 1 | 1 | 1 | 1 | 1 | — | 8 |
| | 2 | 1 | 2 | 3 | 3 | 1 | 1 | 1 | 1 | 1 | 1 | 1 | 1 | 1 | 1 | 1 | 6 | 8 |
| | 1 | 3 | 4 | 5 | 3 | 2 | 1 | 2 | 1 | 1 | 1 | 1 | 1 | 1 | 1 | 2 | 8 | 9 |
| | 0.5 | 3 | 4 | 7 | 6 | 2 | 1 | 3 | 1 | 1 | 1 | 1 | 2 | 1 | 4 | 9 | 9 |
| A | 4 | 1 | 4 | 6 | 2 | 2 | 1 | — | 1 | 1 | 1 | — | — | 1 | 1 | 2 | — | 9 |
| | 2 | 3 | 9 | 7 | 5 | 2 | 1 | — | 1 | 1 | 1 | — | — | 1 | 1 | 3 | — | 9 |
| | 1 | 4 | 9 | 7 | 5 | 2 | 1 | — | 1 | 1 | 1 | — | — | 4 | 1 | 7 | — | 9 |
| | 0.5 | 9 | 9 | 7 | 6 | 2 | 1 | — | 1 | 1 | 1 | — | — | 5 | 1 | 9 | — | 9 |
| B | 4 | 1 | 3 | 5 | 6 | — | 1 | 9 | 1 | 1 | 1 | 4 | 1 | 1 | 1 | 2 | 7 | 8 |
| | 2 | 3 | 7 | 8 | 6 | — | 1 | 9 | 1 | 1 | 1 | 4 | 1 | 2 | 2 | 9 | 8 |
| | 1 | 6 | 9 | 9 | 9 | — | 1 | 9 | 1 | 1 | 1 | 5 | 1 | 2 | 2 | 2 | 9 | 9 |
| | 0.5 | 9 | 9 | 9 | 9 | — | 1 | 9 | 1 | 2 | 1 | 6 | — | 3 | 3 | 3 | 9 | 9 |

The agents according to the invention are manufactured in known manner by intimately mixing and/or grinding the active substance of the formula I with the suitable carriers, optionally with the addition of dispersants or solvents which are inert towards the active substance. The active substance may take and be used in the following forms:

Solid forms:
  dusts, tracking agents, granules, coated granules, impregnated granules and homogeneous granules.
Liquid forms:
  (a) active substances which are dispersible in water: wettable powders, pastes, emulsions;

(b) solutions.

To manufacture solid forms (dusts, tracking agents), the active substance is mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates,, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

The particle size of the carriers for dusts is advantageously up to 0.1 mm, for tracking agents from about 0.075 to 0.2 mm, and for granules 0.2 mm or larger.

The solid forms contain the active substances in concentrations from 0.5% to 80%.

To these mixtures can also be added additives which stabilize the active substance and/or non-ionic, anionic and cationic surface active substances, which for example improve the adhesion of the active ingredients on plants or parts of plants (adhesive and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ether having 5 to 20 ethylene oxide radicals per molecule and 8 to 18 carbon atoms in the fatty alcohol moiety, condensation product of urea and formaldehyde, and also latex products. Preferred dispersions (suspensions and emulsions) are manufactured by mixing or grinding the active substance with carriers accompanied by the addition of dispersing agents and solvents, in the process of which there result firstly dispersible active substance concentrations, such as wettable powders and emulsifiable concentrates.

The water-dispersible concentrates of the active substance i.e. wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents. The active substance concentrations in these agents are from 5-80%.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Suitable anti-foam agents are silicones.

The active substance is so mixed, ground sieved and strained with the additives mentioned above that, in wettable powders, the solid particle size of from 0.02 to 0.04 and in pastes, of 0.03 is not exceeded. To produce emulsifiable concentrates and pastes, dispersing agents such as those given in the previous paragraphs, organic solvents and water are used. Examples of suitable solvents are the following: alcohols, benzene, xylenes, toluene, dimethylsulphoxide, and mineral oil fractions boiling between 120° and 350° C. The solvents must be practically odorless, not phytotoxic, inert to the active substance and not readily inflammable.

Furthermore, the agents according to the invention can be applied in the form of solutions. For this purpose the active substance of formula I is dissolved in suitable organic solvents, mixtures of solvents or in water. Aliphatic and aromatic hydrocarbons, chlorinated derivatives thereof, alkyl naphthalenes and mineral oils singly or in admixture, can be used as organic solvents. The solutions contain the active substance in a concentration range from 1% to 20%.

In addition the agents described according to the invention can be mixed with other biocidally active substances or agents. Thus in order to broaden the activity spectrum the new agents may contain, for example, insecticides, fungicides, bactericides, fungistatics, bacteriostatics or nematocides, in addition to the cited active substance of the formula I. The agents according to the invention may also contain plant fertilisers, trace elements etc.

The active substance of the formula I can, for example, be formulated as follows. The parts denote parts by weight.

Granules

The following substances are used to manufacture 5% granules:
5 parts of 2-chloro-2',6'-dimethyl-N-(2-methoxyethyl)acetanilide,
15 parts of rosin
80 parts of pumice-stone (particle size 0,2–0,6 mm)
The active substance and rosin are dissolved in methylene chloride. The resulting solution is sprayed on pumice-stone and then the solvent is evaporated in vacuo.

Wettable powder

The following constituents are used to manufacture (a) a 70%, (b), a 25% and (c) a 10% wettable powder:
(a)
  70 parts of compound I
  5 parts of sodium dibutylnaphthalene sulphonate,
  3 parts of naphthalenesulphonic acid/phenolsulphonic acid/formaldehyde condensate (3:2:1),
  20 parts of kaolin,
  22 parts of Champagne chalk;
(b)
  25 parts of compound I
  5 parts of oleylmethyltaurid-sodium-salt,
  2.5 parts of naphthalenesulphonic acid/formaldehyde condensate, 0.5 part of carboxymethyl cellulose,
5 parts of neutral potassium-aluminium-silicate,
62 parts of kaolin;
(c)
10 parts of compound I
3 parts of a mixture of the sodium salts of saturated fatty alcohol sulphates,
5 parts of naphthalenesulphonic acid/formaldehyde condensate,
82 parts of kaolin.

The indicated active substance is applied to the corresponding carriers (kaolin and chalk and then these are mixed and ground, to yield wettable powders of excellent wettability and having an excellent capacity for forming suspensions. By diluting these wettable powders with the 10-fold amount of water it is possible to obtain suspensions containing 7%, 2.5% and 1% of active substance.

Paste

The following substances are used to manufacture a 45% paste:
45 parts of compound I
5 parts of sodium aluminium silicate,
14 parts of cetyl polyglycol ether with 8 mols of ethylene oxide,
1 part of oleyl polyglycol ether with 5 mols of ethylene oxide,
2 parts of spindle oil,
10 parts of polyethylene glycol,
23 parts of water.

The active substance is intimately mixed with the addition in appropriate devices and ground. A paste is obtained from which, by diluting it with water, is possible to manufacture suspensions of every desired concentration.

Emulsion Concentrate

To manufacture a 25% emulsion concentrate
25 parts of compound I
5 parts of a mixture of nonylphenolpolyoxyethoxyethylene and calcium dodecylbenzenesulphonate
35 parts of 3,5,5-trimethyl-2-cyclohexan-1-one,
35 parts of dimethyl formamide,
are mixed together. This concentrate can be diluted with water to give emulsions in desired concentrations. Such aqueous emulsions can be used for regulating plant growth and as a dressing agent for stored tubers.

What we claim is:

1. The compound 2-chloro-2',6'-dimethyl-N-(2-methoxyethyl)-acetanilide of the formula

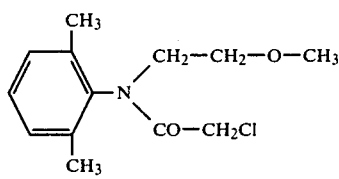

2. An agent for retarding plant growth containing as active substance an effective plant growth retarding amount of the compound as claimed in claim 1, together with one or more suitable carriers.

3. A method of retarding plant growth which comprises applying to plants or parts of plants an effective plant growth retarding amount of the compound as claimed in claim 1.

4. A method according to claim 3 wherein the compound is applied to stored tubers.

* * * * *